(12) United States Patent
Kosugi et al.

(10) Patent No.: US 10,605,771 B2
(45) Date of Patent: Mar. 31, 2020

(54) ELECTROPLATING SOLUTION ANALYZER AND ELECTROPLATING SOLUTION ANALYSIS METHOD

(71) Applicant: TOPPAN PRINTING CO., LTD., Tokyo (JP)

(72) Inventors: Masahiro Kosugi, Tokyo (JP); Toshikazu Okubo, Tokyo (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 11 days.

(21) Appl. No.: 15/843,579

(22) Filed: Dec. 15, 2017

(65) Prior Publication Data
US 2018/0106757 A1  Apr. 19, 2018

Related U.S. Application Data

(63) Continuation of application No. PCT/JP2016/068970, filed on Jun. 27, 2016.

(30) Foreign Application Priority Data

Jun. 29, 2015 (JP) .................................. 2015-129793

(51) Int. Cl.
*C25D 21/12* (2006.01)
*G01N 27/42* (2006.01)
*G01N 27/28* (2006.01)

(52) U.S. Cl.
CPC ............. *G01N 27/42* (2013.01); *C25D 21/12* (2013.01); *G01N 27/28* (2013.01)

(58) Field of Classification Search
None
See application file for complete search history.

(56) References Cited

U.S. PATENT DOCUMENTS 5,223,118 A  6/1993  Sonnenberg et al.
7,291,253 B2  11/2007  Pavlov et al.
(Continued)

FOREIGN PATENT DOCUMENTS

JP  2005-290413  10/2005
JP  2009-299193  12/2009
(Continued)

OTHER PUBLICATIONS

Kosugi, M et al; "The Practical Method for Monitoring Additives in Copper electroplating baths Using the Chronopotentiometry Techniques" ECS Transactions, 66 (20) 1-9 (2015). (Year: 2015).*
(Continued)

*Primary Examiner* — Brian W Cohen
(74) *Attorney, Agent, or Firm* — Foley & Lardner LLP

(57) ABSTRACT

An electroplating solution analyzer includes an analysis container for housing an electroplating solution containing additives including an accelerator and a suppressor, a working electrode that is immersed in the electroplating solution housed in the analysis container to exchange electrons therewith, a reference electrode immersed in the electroplating solution and serves as a reference for determining a potential of the working electrode, a counter electrode immersed in the electroplating solution, a rotation drive unit for rotating the working electrode at a constant speed, a current-generating unit for supplying a current with a constant current density between the working electrode and the counter electrode, a potential measuring unit for measuring a potential between the working electrode and the reference electrode, and an analyzing unit for determining a condition of the electroplating solution in one or more measurement sections at an elapsed time after the current starts to be supplied.

7 Claims, 5 Drawing Sheets

(56) References Cited

U.S. PATENT DOCUMENTS

| | | | | |
|---|---|---|---|---|
| 7,820,535 B2* | 10/2010 | Okubo | ................... | G01N 27/42 |
| | | | | 205/123 |
| 7,879,222 B2 | 2/2011 | Shalyt et al. | | |
| 8,440,555 B2 | 5/2013 | Okubo et al. | | |
| 2016/0377573 A1* | 12/2016 | Kosugi | ................ | G01N 27/423 |
| | | | | 205/81 |

FOREIGN PATENT DOCUMENTS

| | | |
|---|---|---|
| JP | 2015-010991 | 1/2015 |
| JP | 2015-172511 | 10/2015 |
| JP | 2016-114391 | 6/2016 |

OTHER PUBLICATIONS

Toshikazu Okubo, et al., "Electrochemical Monitoring Method for Filing Capability of Copper Electroplating Solution for Via Filling", Journal of Japan Institute of Electronics Packaging (2005), vol. 8, No. 4, pp. 318-324.

International Search Report issued in International Patent Application No. PCT/JP2016/068970 dated Sep. 20, 2016.

* cited by examiner

ELECTROPLATING SOLUTION ANALYZER AND ELECTROPLATING SOLUTION ANALYSIS METHOD

CROSS-REFERENCE TO RELATED PATENT APPLICATIONS

This application is a continuation application filed under 35 U.S.C. § 111(a) claiming the benefit under 35 U.S.C. §§ 120 and 365(c) of International Application No. PCT/JP2016/068970, filed Jun. 27, 2016, which is based upon and claims the benefit of priority of Japanese Patent Application No. 2015-129793, filed Jun. 29, 2015, the entireties of which are hereby incorporated by reference.

TECHNICAL FIELD

The present invention relates to an electroplating solution analyzer and an electroplating solution analysis method, and in particular to an electroplating solution analyzer and electroplating solution analysis method for analyzing an electroplating solution by depositing and growing an electroplating film in a contact via or through-hole (hereinafter referred to as a "via") formed on a high-density mounting substrate, a semiconductor substrate, and a substrate for a semiconductor package, the electroplating solution being used in forming a contact electrode or a through-hole electrode.

BACKGROUND ART

A contact electrode or a through-hole electrode is conventionally formed from an electrolytic copper plating film in an electrolytic plating method by use of an electrolytic copper plating solution, the method depositing and growing an electrolytic copper plating film in a via formed on a high-density mounting substrate, a semiconductor substrate, and a semiconductor package substrate.

In order to improve physical properties and deposition properties of a plating film, an additive such as an accelerator, a suppressor, and a leveler is added to the electrolytic copper plating solution described above.

As an accelerator, SPS (bis (sodiumsulfopropyl) disulfide), for example, is used.

As a suppressor, PEG (poly (ethylene glycol)), for example, is used.

As a leveler, a polyamine, for example, is used.

In order to stabilize the quality of the plating film, it is important to control and adjust amounts of additives contained in the electrolytic copper plating solution (concentrations of the accelerator, suppressor, and leveler). The additive, however, decomposes or degenerates as time elapses from a point of time when a plating reaction starts. Controlling additives therefore requires consideration of this point.

The cyclic voltammetry stripping (CVS) method is generally used to control additives. The CVS method repeatedly changes a potential of a platinum rotating disk electrode at a constant rate in a plating solution. This causes a metal plating film to be repeatedly deposited and dissolved on a surface of an electrode.

The CVS method keeps a potential scanning rate constant. Hence a dissolution peak area on a voltammogram is generally proportional to an average deposition rate, which is closely related to a concentration of an additive in the plating solution.

In the CVS method, preparing a calibration curve of a standard plating solution makes it possible to carry out quantitative analysis of an additive in a sample plating solution.

Conventional CVS devices using the CVS method pose several technical problems. For example, even if the additive in the electrolytic plating solution deteriorates due to decomposition and changes according to a period of time elapsing from the start of a plating reaction, a conventional CVS device includes the amount of deteriorated additive in the additive concentration when analyzing the sample plating solution.

The technique described in PTL 1 is known as an analysis method which considers such degradation of an additive (in other words, decomposition and changes of an additive in an electrolytic copper plating solution).

PTL 1 discloses using the CVS method to analyze MPSA (3-mercaptopropylsulfonic acid), a decomposed product of an SPS that is added as an accelerator.

PTL 2 discloses using the voltammetric method to analyze decomposition products of a leveler component.

The analysis methods disclosed in PTLs 1 and 2, however, pose a problem of requiring complicated operations, though these methods can be carried out with a conventional CVS device. More specifically, these methods require repetitive potential scanning to investigate how a potential varies or to measure two types of plating solutions prepared at different dilution ratios.

The techniques described in PTLs 3 and 4 describe simpler methods of analyzing the effect of decomposition products of additives contained in an electrolytic copper plating solution than the methods described in PTLs 1 and 2.

PTL 3 discloses an analysis method of obtaining an amount of an additive by applying constant current electrolysis to an electrolytic copper plating solution containing a brightener and a leveler as additives to yield a time-potential curve.

PTL 4 discloses an analysis method of determining a state of an electrolytic copper plating solution containing an additive from a time-potential curve yielded by application of constant current electrolysis to the electrolytic copper plating solution.

Carrying out the analysis methods of PTLs 3 and 4 involves using a rotary electrode.

CITATION LIST

Patent Literature

[PTL 1] U.S. Pat. No. 7,291,253
[PTL 2] U.S. Pat. No. 7,879,222
[PTL 3] U.S. Pat. No. 5,223,118
[PTL 4] U.S. Pat. No. 8,440,555

SUMMARY OF THE INVENTION

Technical Problem

The analysis methods disclosed in PTL 3, however, do not clarify how the yielded results and the copper plating deposition properties are related to each other.

In the analysis method disclosed in PTL 4, an approximate expression is applied to a time-potential curve yielded by constant current electrolysis to determine deposition properties of the electrolytic copper plating film to a via from an initial potential-variation rate at the constant current electrolysis and a convergence point of the electric potential.

Depending on differences in types and concentrations of additives, however, the electrolytic copper plating solution provides a variety of time-potential curves when constant current electrolysis is carried out. This may on occasion make it impossible to accurately determine deposition properties of an electrolytic copper plating film from the measurement of an initial potential-variation and a convergence point of an electric potential.

The analysis methods disclosed in PTLs 3 and 4 may on occasion make it impossible to accurately determine a condition of an electroplating solution for depositing an electroplating film in a via on a high-density mounting substrate, a semiconductor substrate, a semiconductor package substrate, or other substrate.

The present invention has been made in view of such problems as described above, and aims to provide an electroplating solution analyzer and an electroplating solution analysis method that can improve accurate determination of a condition of an electroplating solution containing additives including an accelerator and a suppressor.

Solution to Problem

An electroplating solution analyzer according to a first aspect of the present invention includes: an analysis container for housing an electroplating solution containing additives including an accelerator and a suppressor as an analytical sample; a working electrode that is immersed in the electroplating solution housed in the analysis container to exchange electrons therewith; a reference electrode that is immersed in the electroplating solution housed in the analysis container and serves as a reference for determining a potential of the working electrode; a counter electrode that is immersed in the electroplating solution housed in the analysis container; a rotation drive unit for rotating the working electrode at a constant speed; a current-generating unit for supplying a current with a constant current density between the working electrode and the counter electrode; a potential measuring unit for measuring a potential between the working electrode and the reference electrode by use of a constant current electrolytic method; and an analyzing unit for determining, by calculating an analysis value for determination having at least one of a potential-variation rate and an average potential and evaluating the analysis value for determination on a basis of a preset determination condition, a condition of the electroplating solution in one or more measurement sections at an elapsed time after the current starts to be supplied.

Note that, in the present specification, the term "condition of an electroplating solution" refers to a state of the electroplating solution related to deposition performance of an electroplating film on a plating object. The condition of an electroplating solution varies by type and concentration of an additive in the electroplating solution varying in accordance with a usage history of the electroplating solution.

The electroplating solution analysis method according to a second aspect of the present invention determines a condition of an electroplating solution by: immersing a working electrode, a reference electrode, and a counter electrode in an electroplating solution containing additives including an accelerator and a suppressor, and rotating the working electrode at a constant speed; supplying a current with a constant current density between the working electrode and the counter electrode to measure a potential between the working electrode and the reference electrode; calculating an analysis value for determination having at least one of a potential-variation rate and an average potential in one or more measurement sections at an elapsed time after the current starts to be supplied; and evaluating the analysis value for determination on a basis of a preset determination condition.

Advantageous Effects of the Invention

According to the electroplating solution analyzer and electroplating solution analysis method according to the above aspect of the present invention, an analysis value for determination having at least one of a potential-variation rate and an average potential is calculated in one or more measurement sections at an elapsed time at a time of analysis of a relation between the elapsed time and the potential. The analysis value for determination is then evaluated on a basis of a preset determination condition. This achieves an effect that a condition of an electroplating solution containing an additive including an accelerator and a suppressor can be accurately determined.

DESCRIPTION OF THE EMBODIMENTS

Embodiments of the present invention will be described below with reference to the accompanying drawings.

It is to be understood that the embodiments described below are intended to be representative of the present invention and that the present invention is not limited to the embodiments. One of skill in the art would understand that the embodiments described below can be varied to develop modifications that are still within the present invention.

First an electroplating solution analyzer according to an embodiment of the present invention will be described.

Figure 1:
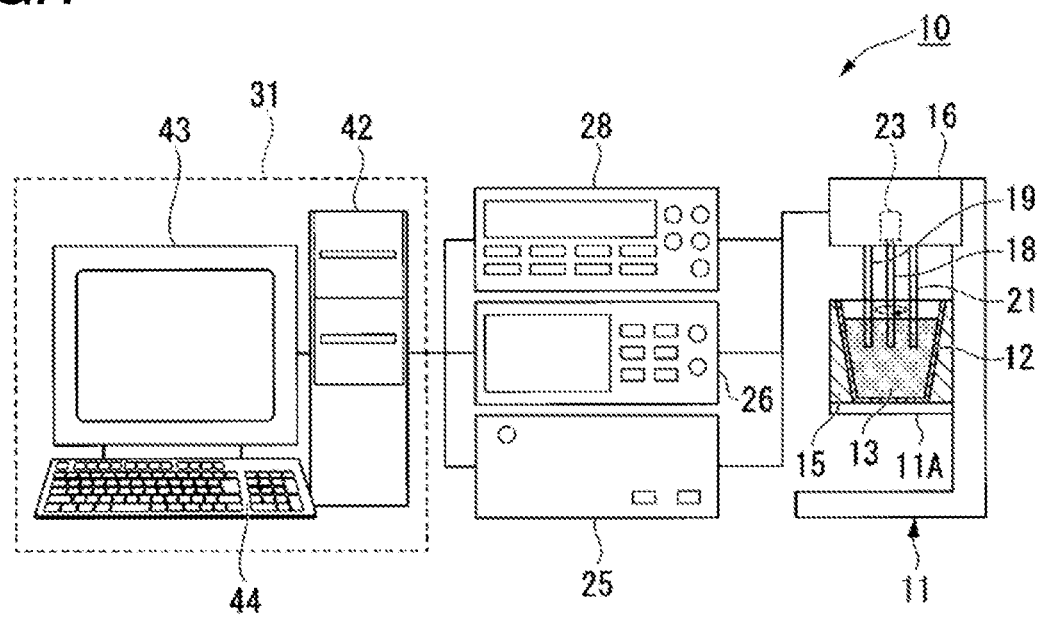
FIG. 1 is a schematic view of an exemplary configuration of an electroplating solution analyzer according to an embodiment of the present invention.

FIG. 1 is a schematic view of an exemplary configuration of the electroplating solution analyzer of the present embodiment.

As shown in FIG. 1, the electroplating solution analyzer 10 of the present embodiment includes a stand 11, an analysis container 12, a temperature holding unit 15, an electrode support unit 16, a working electrode 18, a reference electrode 19, a counter electrode 21, a rotation drive unit 23, a current-generating unit 26, a potential measuring unit 28, a controller 25, and an analyzing unit 31.

The stand 11 has a stage unit 11A on which the analysis container 12 and the temperature holding unit 15 are mounted.

The analysis container 12 is a container for storing an electroplating solution 13 to be analyzed as an analytical sample. The analysis container 12 is disposed on the stage unit 11A of the stand 11.

Examples of the electroplating solution 13 to be analyzed include the electroplating solution 13 used in an appropriate unshown plating device. The object to be analyzed, however, is not limited to a used electroplating solution 13. For example, an unused electroplating solution 13 can be analyzed for the purpose of, for example, obtaining comparative data in a favorably conditioned circumstance.

Now a description will be given of the electroplating solution 13.

The electroplating solution 13 can be composed of a metal ion for electroplating and an additive.

There is no particular restrictions on the types of the metals for electroplating. Examples of metals for electroplating may include copper, nickel and other metals.

The electroplating solution 13 is hereinafter used for electrolytic copper plating unless otherwise stated. In the examples described below, the electroplating solution 13 contains at least the Cu (II) ion.

The additives contained in the electroplating solution 13 contain at least an accelerator and a suppressor. The accelerator has an action that facilitates deposition of the metal ions in the electroplating solution 13 as metal. The suppressor has an effect of inhibiting metal ions in the electroplating solution 13 from depositing as metal.

Additionally, the additive may contain a component exhibiting an action of a leveler. A leveler is a component that contributes to improvement in smoothness of a metal plating film because it weakly acts to inhibit metal deposition.

Each of the accelerator, suppressor, and leveler is often added as a separate compound, but a multi-action compound may be used, the actions being provided by a plurality of functional groups.

As an accelerator, SPS (bis (sodiumsulfopropyl) disulfide) or other sulfur-containing compound can be used.

As a suppressor, a water-soluble polymer, such as polyethylene oxide or polypropylene oxide, or PEG [poly (ethylene glycol)] can be used.

As a leveler, an organic compound such as polyamine, polyacrylic amine, poly (N-methyldiallylamine), poly (N-vinylpyrrolidone), poly (N-vinyl-N'-methylimidazoliumchloride) can be used.

The above-mentioned additives contained in the electroplating solution 13 were supplied alone or in a variety of combinations by a number of suppliers.

The electroplating solution 13 may contain an anion (e.g., sulfate) which serves as a counter ion of the Cu (II) ion, an acid (e.g., sulfuric acid), and a chlorine ion.

The amount of the Cu (II) ions in the electroplating solution 13 can be set in a range of, for example, 2 g/L to 70 g/L. The amount of sulfuric acid can be set in a range of, for example, 10 g/L to 200 g/L. The suitable amount of chlorine ranges, for example, from 1 mg/l to 150 mg/l.

The optimum amount of each of the components may be determined by, for example, a performance evaluation of the electroplating solution 13. The same applies to the concentration of an additive component.

The temperature holding unit 15 is placed on the stage unit 11A so as to surround an outer peripheral surface of the analysis container 12. The temperature holding unit 15 is configured to hold a temperature of the electroplating solution 13 stored in the analysis container 12 at a constant temperature.

The temperature of the electroplating solution 13 may be selected, for example, from 20° C. to 35° C. A±1° C. variation in temperature can be considered to be constant.

A warm water tank, for example, can serve as the temperature holding unit 15.

Having such a temperature holding unit 15 can stabilize accuracy of analysis.

Note that FIG. 1 shows a temperature holding unit 15 surrounding an outer peripheral surface of the analysis container 12, as an example. The temperature holding unit 15 may be, however, configured to cover not only the outer peripheral surface of the analysis container 12 but a bottom surface of the analysis container 12 as well.

The electrode support unit 16 is fixed to an upper end of the stand 11. The electrode support unit 16 is disposed to face a liquid level of the electroplating solution 13 stored in the analysis container 12.

The electrode support unit 16 is a member for supporting rear ends of the working electrode 18, the reference electrode 19, and the counter electrode 21, all of which will be described later.

In the present embodiment, a potential measured by use of the working electrode 18, the reference electrode 19, and the counter electrode 21 varies depending on a positional relation among the working electrode 18, the reference electrode 19, and the counter electrode 21.

A potential is hence preferably measured with the working electrode 18, the reference electrode 19, and the counter electrode 21 being always fixedly positioned. For example, it is undesirable if a positional relation among the working electrode 18, the reference electrode 19, and the counter electrode 21 requires adjustment each time the electroplating solution 13 (analytical sample) is replaced.

Hence in order to measure a more reproducible potential data, the electrode support unit 16 is preferably configured to enable the positional relationship among the working electrode 18, the reference electrode 19 and the counter electrode 21 to be fixed.

The working electrode 18 is supported by the electrode support unit 16 via the rotation drive unit 23, which will be described later, so that an end thereof is immersed in the electroplating solution 13.

The working electrode 18 is an electrode that exchanges electrons with chemical species in the electroplating solution 13.

The reference electrode 19 is supported by the electrode support unit 16 so that an end thereof is immersed in the electroplating solution 13.

The reference electrode 19 is an electrode that serves as a reference in determining a potential of the working electrode 18.

Available as a material of the reference electrode 19 is, for example, saturated calomel ($Hg/Hg_2Cl_2$) and silver/silver chloride (Ag/AgCl).

The counter electrode 21 is supported by the electrode support unit 16 so that an end thereof is immersed in the electroplating solution 13.

The counter electrode 21 is an electrode for supplying a current to the electroplating solution 13 between the counter electrode 21 and the working electrode 18 to cause a reaction on an interface between the counter electrode 21 and the electroplating solution 13.

A copper electrode or a platinum coated titanium electrode, for example, can be used as the counter electrode 21, the copper electrode being a consumable electrode and the platinum coated titanium electrode being a non-consumable electrode.

As for the surface area of the counter electrode 21, a surface area that can be immersed in the electroplating solution 13 is preferably more than or equal to the electrode surface area of the working electrode 18 so as to prevent a flow rate of a total current from being determined by the reaction on the counter electrode 21. More specifically, the surface area that can be immersed in the electroplating solution 13 in the counter electrode 21 is preferably, for example, one to fifty times as large as the surface area of the working electrode 18.

The counter electrode 21 may also be referred to as a counter electrode or an auxiliary electrode.

The rotation drive unit 23 is housed in the electrode support unit 16 and connected to the rear end of the working electrode 18.

The rotation drive unit 23 is configured to rotate the working electrode 18 at a constant speed.

The rotational frequency (rotational speed) of the working electrode 18 carried out by the rotation drive unit 23 can be set in a range of, for example, 10 rpm to 8000 rpm.

Changing the rotational frequency of the working electrode 18 by means of the rotation drive unit 23 changes a diffusion state of an additive in the electroplating solution 13. The rotational frequency and a difference in concentration of each component of the additive, therefore, affects how likely a difference in the measurement data of the potential to be described later is to appear.

It is then preferable to conduct an advance study such as an experiment with different rotational frequencies so as to find out in advance a rotational frequency that makes it relatively easy to see how the measurement data varies depending on compositions of individual components of the additive, and to use the rotational frequency to measure the potential that is described later.

The rotational frequency of the working electrode 18 by means of the rotation drive unit 23 is preferably equal to or greater than 10 rpm, at which an effect of rotation appears. On the other hand, a rotational frequency greater than 8000 rpm is undesirable because the speed is hard to mechanically control.

The current-generating unit 26 is electrically connected to the working electrode 18 and the counter electrode 21.

The current-generating unit 26 is configured to supply a current between the working electrode 18 and the counter electrode 21, a current whose density in the working electrode 18 is held constant.

The current-generating unit 26 is preferably configured to enable, for example, a DC current of 10 A or less and 10 V or less to be controlled in a range of ±10 mV or less relative to a set voltage and in a range of ±10 mA or less relative to a set current.

A DC stabilized power supply, for example, can serve as the current-generating unit 26.

A current density in the working electrode 18 is preferably within a range from of 0.1 $A/dm^2$ to 20 $A/dm^2$, even more preferably within a range of 0.5 $A/dm^2$ to 5 $A/dm^2$.

A current density below 0.1 $A/dm^2$ is less likely to exhibit a difference between measurement results of a potential. Additionally, a current density above 5 $A/dm^2$ is less likely to stabilize a potential.

A potential measuring unit 28 is communicatively connected to the working electrode 18, the reference electrode 19, and the analyzing unit 31, the analyzing unit 31 being described later.

The potential measuring unit 28 is configured to measure a potential between the working electrode 18 and the reference electrode 19 with a current flowing between the working electrode 18 and the counter electrode 21 having a current density which is held constant. Data relating to the potential measured by the potential measuring unit 28 is transmitted to the analyzing unit 31.

The potential measuring unit 28 may be a potentiometer, a voltmeter, a multi-meter or other meter that is capable of measuring a potential with a ±10 mV margin of error during potential measurement.

Note that, before starting to measure a potential, the working electrode 18 is required to be rotating at a constant speed.

A time period during which to measure a potential (hereinafter referred to as a "measurement period $t_m$") is preferably as short as possible within a range where a value of the potential stabilizes.

The measurement period $t_m$ may be set within a range of, for example, 1-40 minutes.

The controller 25 is communicatively connected to the rotation drive unit 23, the current-generating unit 26, and the potential measuring unit 28.

The controller 25 is configured to control the rotation drive unit 23, the current-generating unit 26, and the potential measuring unit 28.

Note that the controller 25, the current-generating unit 26, and the potential measuring unit 28 may be individually separate or mutually integrated as one unit, as shown in FIG. 1.

The controller 25 may also be integrated with an analyzing unit 31, which is described later.

The analyzing unit 31 has a main analyzing body 42, a display 43 for displaying an analysis result, a keyboard 44, and a mouse (not shown). The device configuration of the analyzing unit 31 may be, for example, a computer such as a personal computer, that is, a computer with a CPU, a memory, an input/output interface, an external storage device, etc.

The main analyzing body 42 is communicatively connected to the controller 25, the current-generating unit 26, the potential measuring unit 28, the display 43, and the keyboard 44 or the mouse (not shown).

The main analyzing body 42 may be communicatively connected to the rotation drive unit 23 so as to be able to control the rotational speed of the working electrode 18.

The main analyzing body 42 stores a program for controlling the controller 25, the current-generating unit 26, the potential measuring unit 28 and the display 43, and a program for carrying out the electroplating solution analysis method of the present embodiment described later.

The main analyzing body 42 can carry out various items of control and data analysis by running these programs.

The main analyzing body 42 preferably has a function of integrating individual functions related to measurement and analysis of a potential to control a series of measurement and analysis.

In a circumstance where the main analyzing body 42 is connected to the rotation drive unit 23, the main analyzing body 42 may store a program for controlling the rotation drive unit 23.

Examples of data analysis carried out by the main analyzing body 42 include calculation of an analysis value for determining a condition of the electroplating solution 13 on a basis of data of a potential measured by the potential measuring unit 28.

The analysis value for determination includes at least one of a potential-variation rate and an average potential in one or more measurement sections in a range of a measurement period $t_m$.

Further examples of the data analysis carried out by the main analyzing body 42 include analysis for determining a condition of the electroplating solution 13 by evaluating an analysis value for determination on a basis of a predetermined determination condition.

A type of the analysis value for determining a condition of the electroplating solution 13, a measurement section for calculating an analysis value for determination, and a condition on the analysis value for determination are, as described later, stored in the analyzing unit 31 by the time the determination is made.

Details of the control and data analysis carried out by the analyzing unit 31 will be described along with a description of how the electroplating solution analyzer 10 works.

Now a description will be given of how the electroplating solution analyzer 10 works according to the present embodiment with a focus on the electroplating solution analysis method of the present embodiment.

Figure 2:
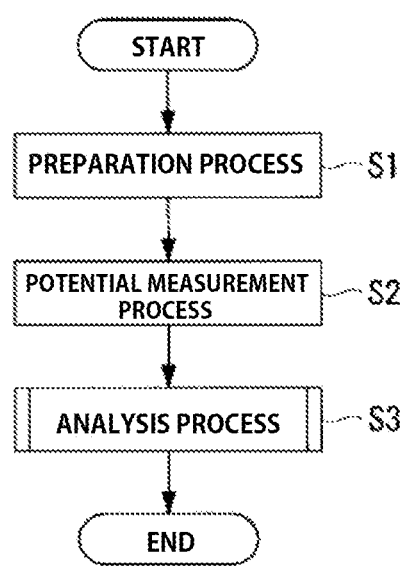
FIG. 2 is a flowchart of an electroplating solution analysis method according to an embodiment of the present invention.
Figure 3:
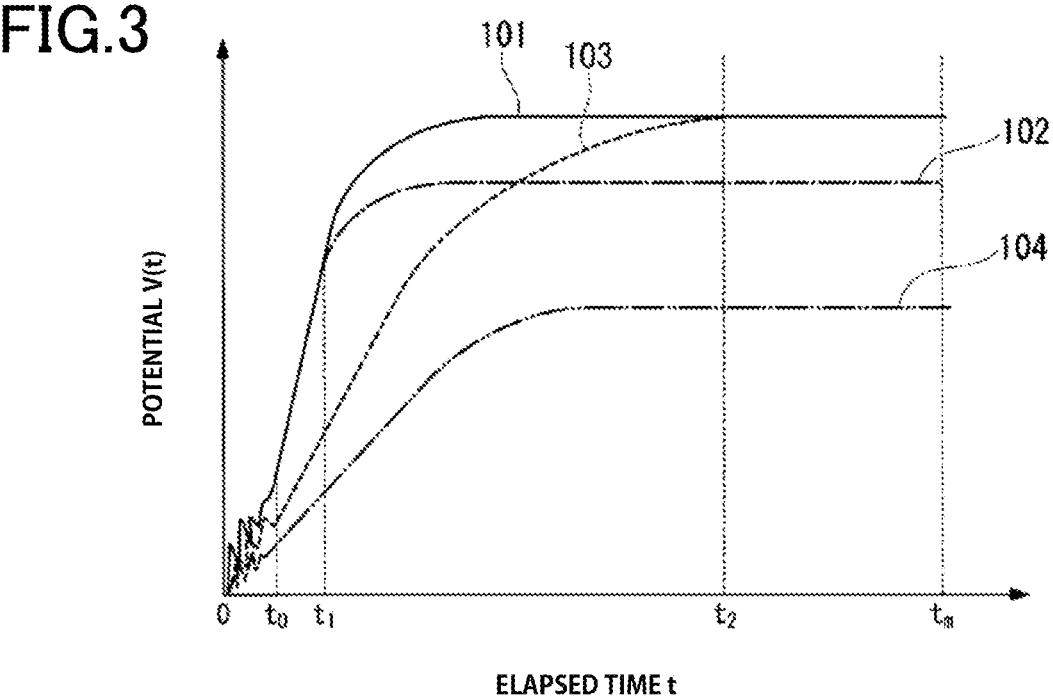
FIG. 3 is a schematic graph of an exemplary potential variation in an electroplating solution measured by an electroplating solution analyzer according to an embodiment of the present invention.
Figure 4:
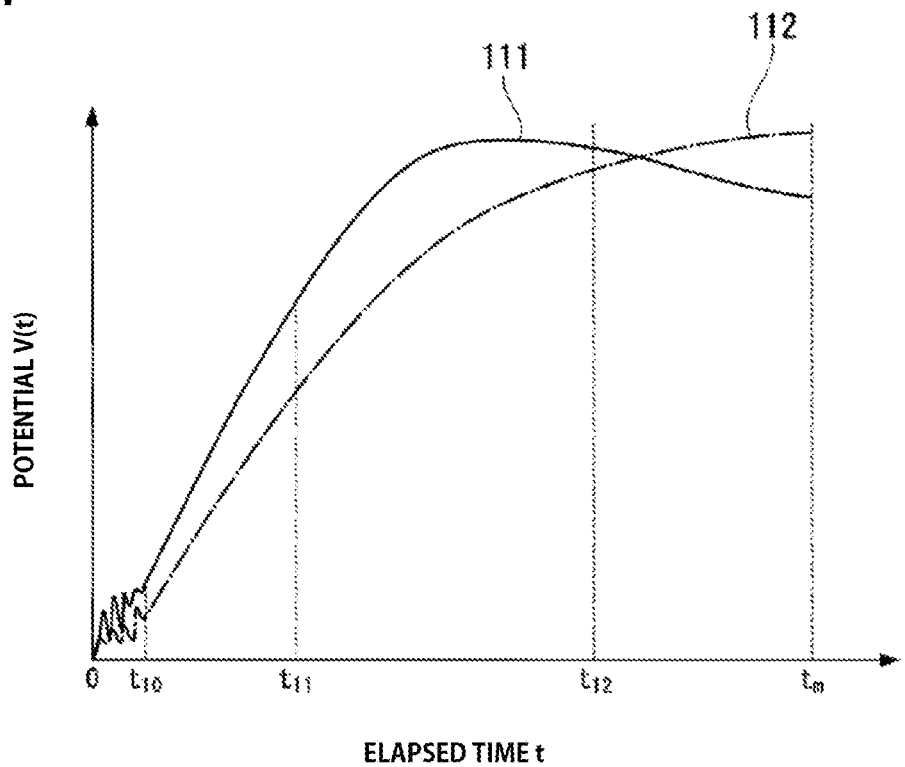
FIG. 4 is a schematic graph of an exemplary potential variation in an electroplating solution measured by an electroplating solution analyzer according to an embodiment of the present invention.
Figure 5:
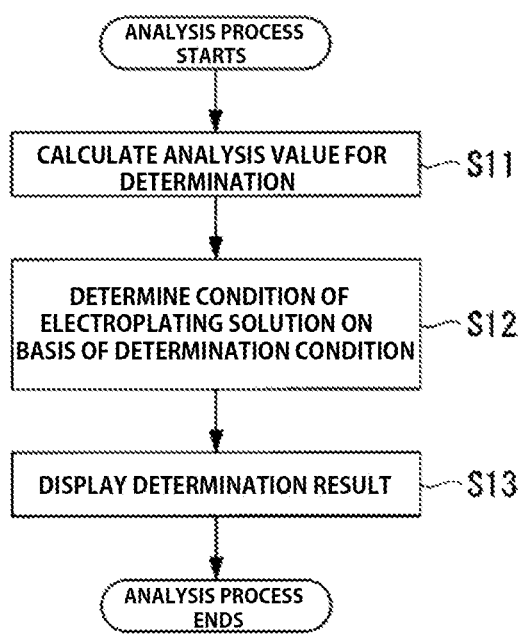
FIG. 5 is a flowchart of analysis steps in an electroplating solution analysis method according to an embodiment of the present invention.

FIG. 2 is a flowchart of the electroplating solution analysis method of the present embodiment. FIGS. 3 and 4 are schematic graphs of an example of a potential variation in an electroplating solution measured by the electroplating solution analyzer of the present embodiment. FIG. 5 is a flowchart of analysis steps of the electroplating solution analysis method of the present embodiment.

Determining a condition of the electroplating solution 13 by means of the electroplating solution analyzer 10, an electroplating solution 13 used in an appropriate plating device (not shown), follows Steps S1 to S3 shown in FIG. 2 in this order. Steps S1 to S3 constitute a preparation process, a potential measurement step, and an analysis step, respectively, of the electroplating solution analysis method of the present embodiment.

In Step S1, the preparation process is carried out. This is a process of immersing the working electrode 18, the reference electrode 19, and the counter electrode 21 in the electroplating solution 13 and rotating the working electrode 18 at a constant speed.

First, a condition for calculating an analysis value for determination (a type and measurement section of the analysis value for determination) required in Step S3, which is described later, will be input to the analyzing unit 31. This input operation, however, may be carried out at any time before the later-described Step S3 starts. This input operation can be carried out via an input interface as appropriate.

For example, in a circumstance where a condition for calculating an analysis value for determination corresponding to the type of the electroplating solution 13 to be analyzed is stored in the analyzing unit 31 in advance, the analyzing unit 31 may display a selection menu on the display 43 to allow an operator of the electroplating solution analyzer 10 to make a selection input.

For example, information associated with a type of the electroplating solution 13 to be analyzed may be recorded by means of a character, a bar code, etc. in a delivery container or a data sheet for the electroplating solution 13 to be analyzed.

On this occasion, causing the analyzing unit 31 to read the information recorded in the delivery container or the data sheet may enable the analyzing unit 31 to automatically select a condition for calculating the analysis value for determination.

Additionally, on an occasion when a condition for calculating a new analysis value for determination is required according to a type of the electroplating solution 13, the operator of the electroplating solution analyzer 10 may directly or interactively enter the new calculation condition.

Then the operator supplies the electroplating solution 13 in the analysis container 12 and places it in the temperature holding unit 15.

Subsequently, the operator immerses the working electrode 18, the reference electrode 19, and the counter electrode 21 into the electroplating solution 13.

When the temperature of the electroplating solution 13 becomes substantially constant, the operator operates the controller 25 to rotate the rotation drive unit 23 at a constant speed that is predetermined for analysis. The working electrode 18 supported by the rotation drive unit 23 thereby starts to rotate at the constant speed. The rotation of the working electrode 18 increases the temperature of the electroplating solution 13, but the temperature becomes constant over time by an action of the temperature holding unit 15.

Note that, in a circumstance where the main analyzing body 42 of the analyzing unit 31 is capable of controlling the rotation drive unit 23, the operation can be carried out through the main analyzing body 42.

Step S1 terminates when the temperature of the electroplating solution 13 becomes constant.

The potential measurement is then carried out in Step S2. This is a process of supplying a current with a constant density between the working electrode 18 and the counter electrode 21 and measuring a potential between the working electrode 18 and the reference electrode 19.

In this process, operating the keyboard 44 or the mouse causes the main analyzing body 42 to start a data analysis program and start a potential measurement.

A control signal is thereby transmitted from the main analyzing body 42 to the current-generating unit 26 and the current-generating unit 26 to actuate these units and start the potential measurement. Alternatively, the control signal may be transmitted from the main analyzing body 42 through the controller 25 to the current-generating unit 26 to actuate the current-generating unit 26 and the potential measuring unit 28 and start the potential measurement.

In other words, the current-generating unit 26 supplies a current with a constant current density between the working electrode 18 and the counter electrode 21, and the potential measuring unit 28 measures a potential.

The potential measurement is carried out for a predetermined measurement period $t_m$ at appropriate time intervals. Then measurement data on V(t), which is a potential at an elapsed time t after the current flow is started, is obtained.

The measurement may be carried out at equal or unequal intervals. The following describes an occasion when the measurement is carried out at intervals of a constant value P.

Data on the potential V(t) measured by the potential measuring unit 28 is transmitted to the analyzing unit 31.

Upon receiving the measurement data of the potential V(t), the analyzing unit 31 displays a graph of the measurement data of the display 43.

Step S2 now terminates.

Here is a description of a relation between a temporal variation in the potential V(t) and a condition of the electroplating solution 13.

FIG. 3 schematically shows exemplary measurement data of the potential V(t) with curves 101, 102, 103, and 104, the data being measured after use of electroplating solutions 13. The electroplating solutions 13 have identical components in an unused state, or in a state before being used.

The temporal variations in the potential V(t) are different because conditions of the respective electroplating solutions 13 on metal deposition are different depending on usage histories of the electroplating solutions 13.

In the example shown in FIG. 3, each potential V(t) tends to show an unstable variation between elapsed times 0 and $t_0$ and thereafter a substantially linear increase, followed by a gradual convergence toward a saturation potential.

The measurement data between the elapsed times 0 and $t_0$ is not used to determine a condition of each electroplating solution 13 because it is hard to understand various conditions from the data. Hence the measurement data of the potentials V(t) below exclude the data between the elapsed times 0 and $t_0$, unless otherwise stated.

During an initial measurement period of time (hereinafter simply referred to on occasion as an initial period) when the potential V(t) increases substantially linearly, metal deposition is apparently promoted by a suppressor adsorbed on a surface of the working electrode 18 being replaced with an accelerator.

In a middle measurement period of time (hereinafter simply referred to on occasion as a middle period), however, the suppressor adsorbed on a surface of the working electrode 18 is more slowly replaced with an accelerator. The suppressor and accelerator adsorbed on the electrode surface then come closer to balance. An excessive amount of accelerator in the electroplating solution 13 at this time apparently results in lower via embeddability.

Improving the via embeddability requires a higher concentration of the accelerator in the via. An excessive amount of accelerator, however, provides a small difference in concentration of the accelerator between the inside and outside of the via, which results in lower via embeddability.

An electroplating solution 13 that provides an excessive accelerator concentration at a time of actual use shifts the potential V(t) of the measurement data in a positive direction, compared with a preferable electroplating solution 13.

In a late measurement period of time (hereinafter simply referred to on occasion as a late period), an amount of the accelerator near the working electrode 18 and a coating amount of the electrode surface are balanced. As a result, the potential difference required to carry out constant current electrolysis becomes substantially constant, which in turn substantially saturates a value of the potential V(t).

For example, the temporal potential variation indicated by the curve 101 shows a high potential-variation rate during the initial period and reaches a saturation of the potential V(t) relatively early.

In this circumstance, metal deposition rapidly proceeds early in a beginning of electroplating. However, because the potential V(t) saturates in a short time, a metal deposition amount does not increase thereafter even when the elapsed time t increases. This makes it hard to control a deposition amount of a metal plating film in the temporal potential variation indicated by the curve 101.

For example, on an occasion when a via is subject to deposition bottom-up deposition, using an electroplating solution 13 whose potential V(t) provides such a temporal variation as indicated by the curve 101 results in lower via embeddability, which leaves an excessively small amount of metal deposition in the vias. Hence the electroplating solution 13 whose potential V(t) provides such a temporal variation as indicated by the curve 101 is not in a good condition.

For example, the temporal potential variation indicated by the curve 102 shows a potential-variation rate identical to that of the curve 101 during the initial period, but shows a saturation value of the voltage V(t) during the late period that is smaller than that of the curve 101.

In this circumstance, metal deposition properties during the late period are better than that of the curve 101. The electroplating solution 13 whose potential V(t) shows such a temporal variation as indicated by the curve 102 is hence considered to be in a condition better than the electroplating solution 13 showing such a temporal variation as indicated by the curve 101.

For example, the temporal potential variation indicated by the curve 103 shows a potential-variation rate lower than that of the curve 101 during the initial period, but shows a saturation value of the voltage V(t) during a late period that is equal to that of the curve 101.

It takes such an electroplating solution 13 longer than the curve 101 before the suppressor adsorbed on the surface of the working electrode 18 and the accelerator become balanced. The electroplating solution 13 whose potential V(t) shows such a temporal variation as indicated by the curve 103 is hence considered to be in a condition better than that of an electroplating solution 13 showing such a potential variation as indicated by the curve 101.

For example, the temporal potential variation indicated by the curve 104 shows a potential-variation rate lower than that of the curve 101 during the initial period, and also shows a saturation value of the voltage V(t) during the late period that is lower than that of the curve 101.

The electroplating solution 13 whose V(t) shows such a temporal variation as indicated by the curve 104 is hence considered to be in a condition better than that of the electroplating solution 13 showing such a temporal variation as indicated by the curve 101.

However, an excessively low potential-variation rate during the initial period means that the suppressor adsorbed on the electrode surface of the working electrode 18 is replaced with the accelerator at a low rate. In this circumstance, the excessive presence of the suppressor in the electroplating solution 13 excessively exhibits an effect that metal deposition is restrained.

Hence in a circumstance where the potential-variation rate during the initial period is too low, the electroplating solution 13 is not in a good condition.

As described above, in a circumstance where a potential V(t) provides a temporal variation that shows a substantially linear increase during the initial period before showing a slower increase, followed by a saturation during the late period, using at least one of the potential-variation rate during the initial period and an average potential during the late period as an analysis value for determination makes it possible to determine a condition of the electroplating solution 13.

Instead of a potential saturation value, an average potential during the late period is used as an analysis value for determination to eliminate an effect of a margin of error caused by a variation in a measured value.

Whether a condition of the electroplating solution 13 can be determined only from a potential-variation rate during the initial period, only from an average potential during the late period, or from a combination of a potential-variation rate during the initial period and an average potential during the late period depends on what electroplating solution 13 and the additives are composed of.

Specific determination conditions may be set empirically by use of samples of electroplating solutions 13 in various use states to carry out electroplating for evaluation of an effect of a condition thereof on metal deposition and measurement of a potential V(t) of each sample.

A period of time during which the potential V(t) changes substantially linearly in an electroplating solution 13 to be analyzed, which has various conditions, is selected as the initial period of time during which to obtain a potential-variation rate. In a circumstance where the potential V(t) in a electroplating solutions 13 to be analyzed, the solutions being in different conditions, changes substantially linearly between $t_0$ and $t_1$, a potential-variation rate can be determined in the measurement section from $t_0$ to $t_1$.

A period of time during which the potential V(t) is substantially constant in the electroplating solutions 13 to be analyzed, the solutions being in various conditions, is selected as the late period of time for calculating an average potential. In a circumstance where the potential V(t) in an electroplating solution 13 to be analyzed, which in a different condition, is substantially constant between $t_2$ and $t_m$, an average potential can be determined in the measurement section from $t_2$ to $t_m$.

On the other hand, a different type or composition of an additive in the electroplating solution 13 may possibly provide a different tendency in temporal potential variation V(t) to be measured in Step S2.

FIG. 4 schematically shows exemplary measurement data of the potential V(t) for such a different electroplating solution 13 with curves 111 and 112. The curves 111 and 112 are exemplary measurement data of the potential V(t) after use of an electroplating solution 13 having an identical component at a time compared to when they are unused.

The curves 111 and 112 show different temporal variations from each other because conditions on metal deposition are different depending on usage histories of respective electroplating solutions 13.

In the example shown in FIG. 4, both potentials V(t) indicated by the curves 111 and 112 tend to show an unstable change between the elapsed times 0 and $t_{10}$ and thereafter a substantially linear increase along with an increase in the elapsed times t before a gradual change in the increase rate, followed by a convergence toward a saturation potential.

However, in the range of the measurement times $t_{12}$ to $t_m$, both potentials V(t) vary gradually toward a saturation potential that is not yet apparent. With regard to the temporal variation in a middle measurement period, the curve 112 shows a monotonical increase, whereas the curve 111 shows a downturn after an increase.

Such a temporal variation may possibly occur, for example, in a circumstance where at least one of the suppressor and the accelerator in an additive of an electroplating solution 13 has a plurality of components with different reaction rates, and a concentration ratio of each component varies depending on usage histories.

In such a circumstance as where a temporal variation pattern of the potential V(t) is hard to determine, calculating at least one of the potential-variation rate and the average potential in a plurality of measurement sections at the elapsed time t can determine more accurately the condition of the electroplating solution 13.

In the measurement section from elapsed times $t_{10}$ to $t_{11}$, which is an initial measurement period, the potentials V(t) indicated by the curves 111 and 112 show a substantially linear increase as the elapsed time t increases. The curve 111 shows a potential-variation rate that is higher than the curve 112 shows.

In the measurement section from elapsed times from $t_{11}$ to $t_{12}$, which is a middle measurement period, the potential V(t) indicated by the curve 111 shows, as the elapsed time t increases, a downturn after a gradual increase. On the other hand, the potential V(t) indicated by the curve 112 gradually increases monotonically as the elapsed time t increases. In the measurement section from the elapsed time $t_{11}$ to $t_{12}$, therefore, the curve 111 shows a potential-variation rate lower than the curve 112.

In this measurement section, the potential V(t) indicated by the curve 112 is characteristically lower than the potential V(t) indicated by the curve 111. The curve 111 hence shows an average potential that is higher than the curve 112.

In a measurement section from elapsed times $t_{12}$ to $t_m$, which is a late measurement period, the potential V(t) indicated by the curves 111 shows, as the elapsed time t increases, a gradual decrease toward saturation. On the other hand, the potential V(t) indicated by the curve 112 gradually increases toward saturation as the elapsed time t increases.

In this measurement section, the potential-variation rate and the average voltage of each potential V(t) indicated by the curves 111 and 112 have magnitude relations opposite to those in the measurement section from $t_{11}$ to $t_{12}$.

It is determined empirically which is in a better condition between the electroplating solutions 13 that yielded the measurement data indicated by the curves 111 and 112.

According to the consideration of the variation of FIG. 3 described above, however, the curve 112 may be possibly in a better condition qualitatively regarding the potential variation during the middle period of measurement, whereas during the late period of measurement, the curve 111 may be in a better potential variation condition.

Hence in this circumstance, considering the potential variation in the middle period of measurement, as well as the potential variations during the initial and late periods of measurement, can improve accuracy of determining the condition.

Obtaining an analysis value for determination in a plurality of measurement sections has been illustratively described as above by use of three measurement sections: the initial, middle, and late periods. However, four or more measurement sections are also allowed. Additionally, the plurality of measurement sections may overlap one another.

Now return to a description of how the electroplating solution analyzer 10 operates.

As shown in FIG. 2, an analysis process is carried out in Step S3. This is a process of analyzing a relation between the elapsed time t and the potential V(t) after starting to supply a current between the working electrode 18 and the counter electrode 21.

This process is automatically started by the analyzing unit 31 after all the data measured by the potential measuring unit 28 is sent to the analyzing unit 31 during the measurement time $t_m$.

As described above, a temporal potential variation V(t) represents a degree of progress of a metal deposition reaction in the electroplating solution 13, and reflects a temporal variation in acceleration and suppression effects of the metal deposition reaction achieved by the additive and others in the electroplating solution 13.

This makes it possible to determine a condition of the electroplating solution 13 from a characteristic of the temporal variation in the potential V(t).

This step is carried out by carrying out the Steps S11 to S13, which are described in FIG. 5, in the stated order.

Step S11 is a step in which the analyzing unit 31 calculates an analysis value for determination.

The analyzing unit 31 uses the measurement data of the potential V(t) sent from the potential measuring unit 28 to calculate an analysis value for determination on a basis of a pre-input condition for calculating an analysis value for determination.

The main analyzing body 42 of the analyzing unit 31 stores an analysis program for calculating an analysis value for determination on a basis of the condition for calculating an analysis value for determination.

There are no particular restrictions on the analysis method for the analysis program.

For example, on an occasion of calculation of respective potential-variation rates $\Delta_j$, as analysis values for determination, from the measurement data of the $n_j$ (where $n_j$ is an integer of 2 or greater) potentials V(t) included in J (where J is an integer of 1 or greater) measurement sections $[t_{Sj}, t_{Ej}]$ (where j=1, ..., J), the following equations (1) and (2) may be used.

[Equation 1]

$$\Delta_j = \frac{V(t_{Ej}) - V(t_{Sj})}{t_{Ej} - t_{Sj}} \quad (1)$$

$$t_{Ej} = t_{Sj} + (n_j - 1) \times P \quad (2)$$

For example, the potential-variation rate $\Delta_j$ may be an inclination of a regression line calculated by a primary regression analysis by use of the least-squares method on the measurement data of the potential V(t) in the measurement section $[t_{Sj}, t_{Ej}]$.

For example, on an occasion of calculation of respective average potentials $\mu_k$, as analysis values for determination, from the measurement data of the $n_k$ (where $n_k$ is an integer of 2 or greater) potentials V(t) included in K (where K is an integer of 1 or greater) measurement sections $[t_{Sk}, t_{Ek}]$ (where k=1, ..., K), the following equations (3), (4), and (5) may be used.

[Equation 2]

$$\mu_k = \frac{\sum_{i=1}^{n_k} V(t_i)}{n_k} \quad (3)$$

$$t_i = t_{Sk} + (i - 1) \times P \quad (4)$$

$$t_{Ek} = t_{Sk} + (n_k - 1) \times P \quad (5)$$

When all the analysis values for determination are calculated by the main analyzing body 42, Step S11 terminates.

In the following description, S (where S=J+K) analysis values for determination are denoted by $E_s$ (s=1, ..., S).

Step S12 is then carried out. This is a step in which the analyzing unit 31 determines a condition of the electroplating solution 13 on a basis of a determination condition.

The main analyzing body 42 evaluates the analysis values for determination Es on a basis of the determination condition stored in the analyzing unit 31 upon completing the calculation of the analysis values for determination $E_s$.

The determination condition defines an individual numerical range $R_s$ [$R_{smin}$, $R_{smax}$] (where $R_{smin} < R_{smax}$) are for each analysis value for determination $E_s$.

The main analyzing body 42 first evaluates whether or not all of the calculated analysis values for determination $E_s$ fall within the numerical value range $R_s$ [$R_{smin}$, $R_{smax}$], and then calculates an individual evaluation value $EV_s$ for each of the analysis value for determinations $E_s$. The individual evaluation value $EV_s$ takes a logical value T (true) or F (false). $EV_s$=T in a circumstance where the analysis value for determination $E_s$ falls within the numerical range $R_s$ [$R_{smin}$, $R_{smax}$], and $EV_s$=F in a circumstance where the analysis value for determination $E_s$ falls outside the numerical range $R_s$ [$R_{smin}$, $R_{smax}$].

Additionally, the determination condition defines a condition for evaluating an overall evaluation value $EV_T$ on a basis of a combination of the individual evaluation values $EV_s$.

The electroplating solution 13 may be determined to be in a good condition if the number, which is represented by T, of individual evaluation values $EV_s$ is larger than or equal to a threshold value.

Alternatively, the electroplating solution 13 may be determined to be in a good condition if a combination pattern of the logic values of the individual evaluation value $EV_s$ matches one or more specific pattern. For example, in a circumstance where S=3 and a combination pattern is expressed as ($EV_1$, $EV_2$, $EV_3$), (T, T, T) and (T, T, F) may be determined to be good, and the other combinations to be poor.

Determining the analysis values for determination $E_s$ calculated by the main analyzing body 42 on a basis of the determination condition terminates Step S12.

Step S13 is then carried out. This is a step in which the electroplating solution analyzer 10 displays a determination result.

The main analyzing body 42 causes the display 43 to display the determination result.

There are no particular restrictions on the display format. For example, the display 43 may display whether the condition is good or not, in addition to the analysis values for determination $E_s$, an individual evaluation value $EV_s$, and a determination condition, or may display only whether the condition is good or not.

Now Step S13 terminates, which means that Step S3 shown in FIG. 2 terminates.

According to the electroplating solution analyzer 10 of the present embodiment and the electroplating solution analysis method by use of the electroplating solution analyzer 10, a condition of the electroplating solution 13 can be determined on a basis of measurement data on a potential V(t) measured by a constant current electrolysis method.

In the present embodiment, at a time of analysis of a relation between an elapsed time t and a potential V(t), an analysis value for determination $E_s$ including at least one of a potential-variation rate $\Delta_j$ and an average potential $\mu_k$ is calculated in one or more measurement sections at the elapsed time t. The analysis value for determination is then evaluated on a basis of a preset determination condition.

Hence, even in a circumstance where the potential V(t) varies intricately depending on a condition of the electroplating solution 13, characteristics of the variation related to metal deposition can be determined more accurately than in a circumstance where the variation in the potential V(t) is analyzed on an assumption of a particular variation curve.

For example, according to PTL 4, which is described above, applying an approximate expression to a potential variation measured by the constant current electrolysis method yields a potential-variation rate during an initial period and a convergence point during a late period as an analysis value for determination. Such a method applies measurement data to the approximate expression even if the measured temporal potential variation cannot be well approximated with an approximate expression, possibly resulting in a larger margin of error of the analysis value itself.

In an electroplating solution containing additives including an accelerator and a suppressor, a reaction mechanism unique to the accelerator and the suppressor differentiates a metal deposition rate. Additionally, changes in concentration of the accelerator and the suppressor in the reaction process also differentiate the metal deposition rate. It is therefore difficult to obtain an approximate expression that can satisfactorily approximate a temporal potential variation for a variety of types and concentrations of accelerators and suppressors.

Additionally, using a specific approximate expression limits the number of analysis values to be yielded. For example, PTL 4, which is described above, limits the analysis values to two: a potential-variation rate during the initial period and a convergence point of a potential during the late period.

With regard to the condition of the electroplating solution 13, however, a difference in the potential variation during the middle measurement period may provide different metal deposition properties, as described above.

The present embodiment makes it possible to yield a plurality of analysis values for determination in one or more measurement sections without finding a single approximate expression. This in turn makes it possible to determine accurately a condition of the electroplating solution 13 even if the electroplating solution 13 provides a complicated temporal variation in the potential V(t) due to the condition thereof, as an electroplating solution 13 containing an additive including an accelerator and a suppressor does.

Note that the description of the above embodiment refers, as an example, to an occasion of use of an electroplating solution analyzer 10 provided separately from a plating device (not shown). For example, however, a plating tank (not shown) of the plating device and the analysis container 12 shown in FIG. 1 may be connected to each other with a line (not shown) to guide an electroplating solution 13 in the plating tank into the analysis container 12 therethrough.

The description of the above embodiment refers to an example in which a binomial determination is made as to whether an electroplating solution is in a good condition or not. However, the condition of the electroplating solution may be multinomially determined to be, for example, very good, good, usable, and unusable.

Although the preferred embodiments of the present invention have been described above, the invention is not limited to these embodiments and modifications thereof. Addition, omission, substitution, and other changes of a configuration can be made without departing from the spirit of the invention.

Additionally, the invention is not limited by the foregoing description but only by the appended claims.

EXAMPLES

Examples 1 to 5 of the foregoing embodiment will be described below, but the present invention is not limited in any way to the following examples.

Figure 6:
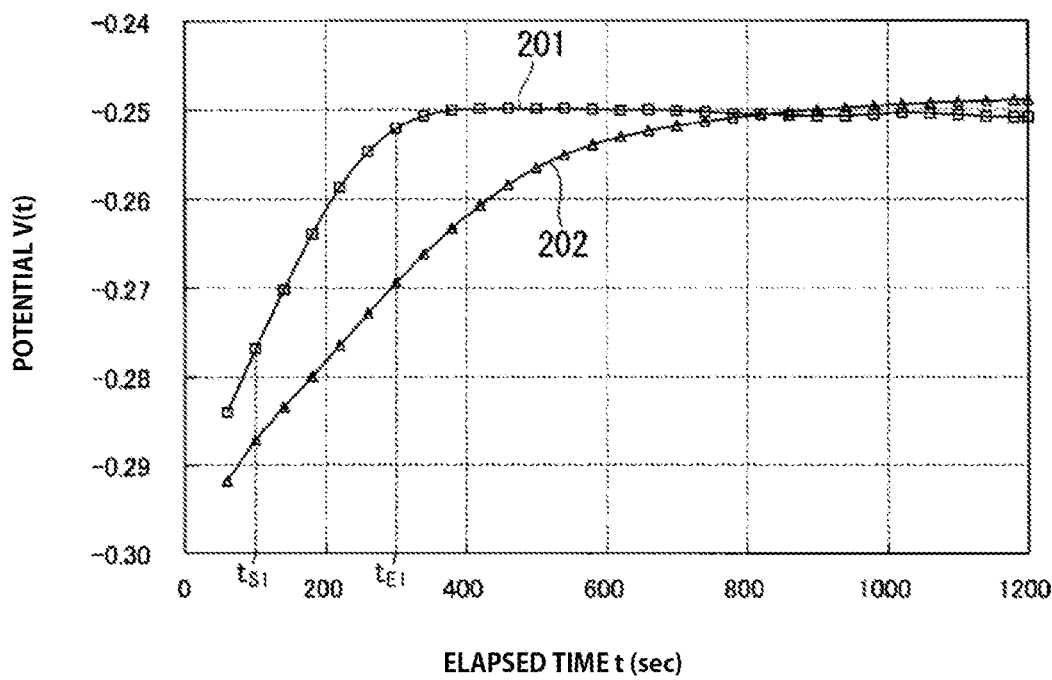
FIG. 6 is a schematic graph of a potential variation in the electroplating solution of Example 1.
Figure 7:
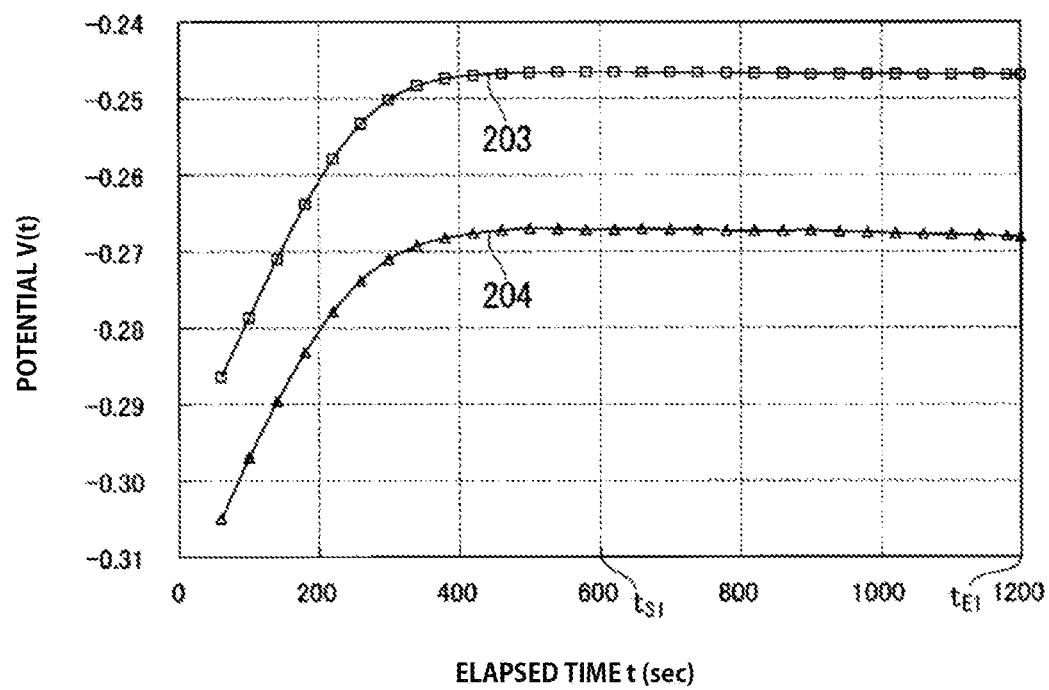
FIG. 7 is a schematic graph of a potential variation in the electroplating solution of Example 2.
Figure 8:
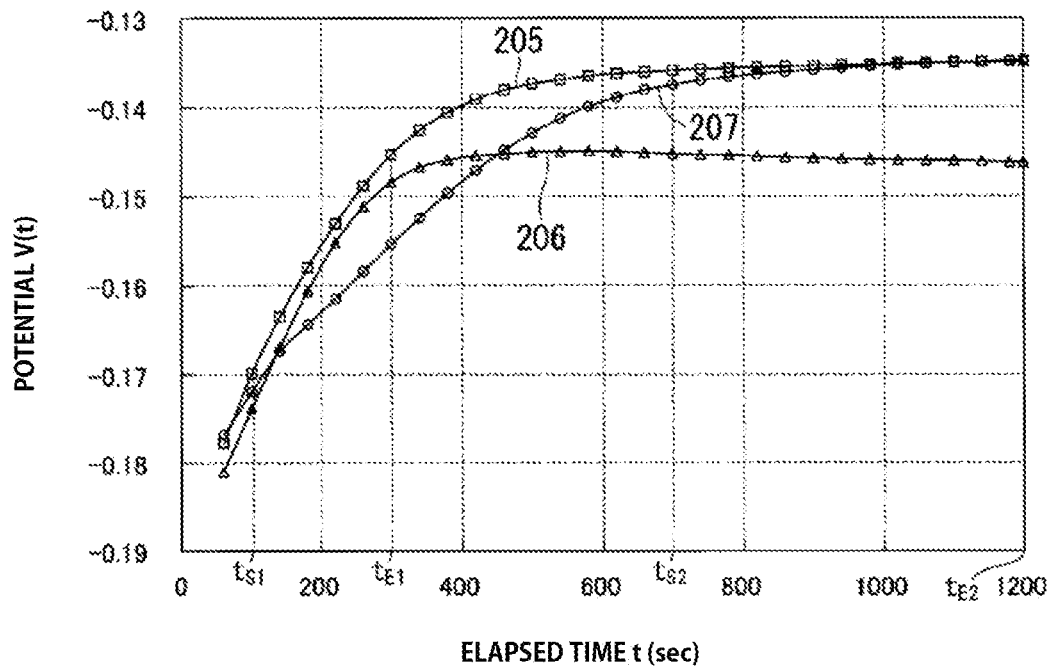
FIG. 8 is a schematic graph of a potential variation in the electroplating solution of Example 3.
Figure 9:
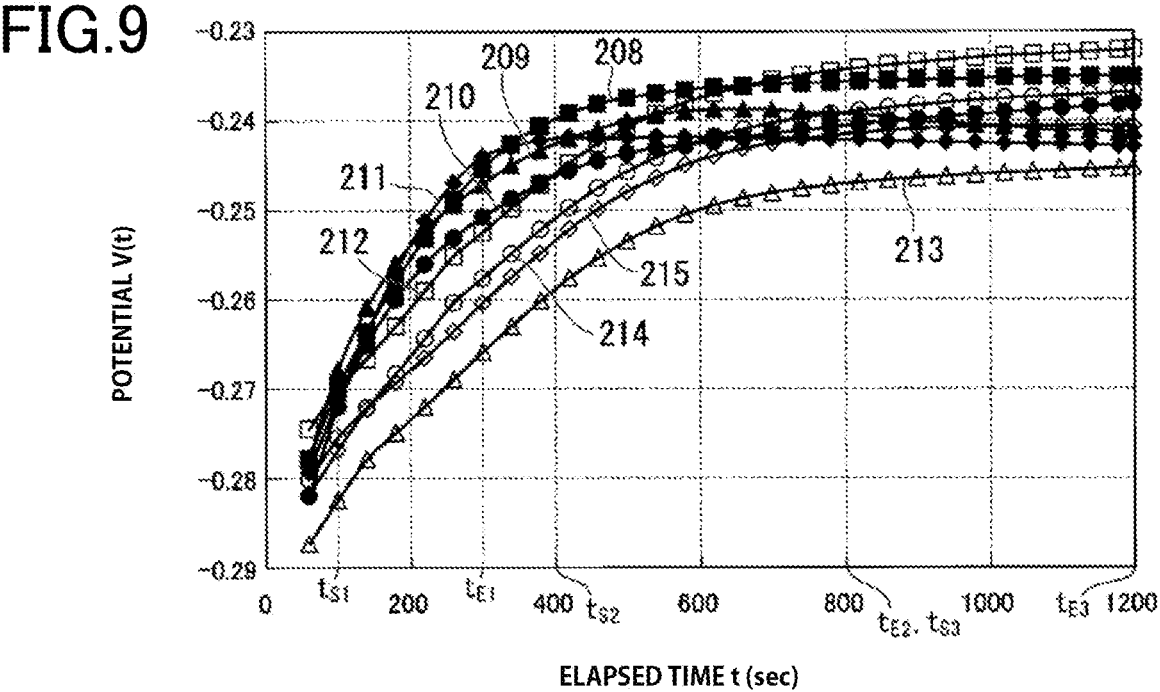
FIG. 9 is a schematic graph of a potential variation in the electroplating solution of Example 4.
Figure 10:
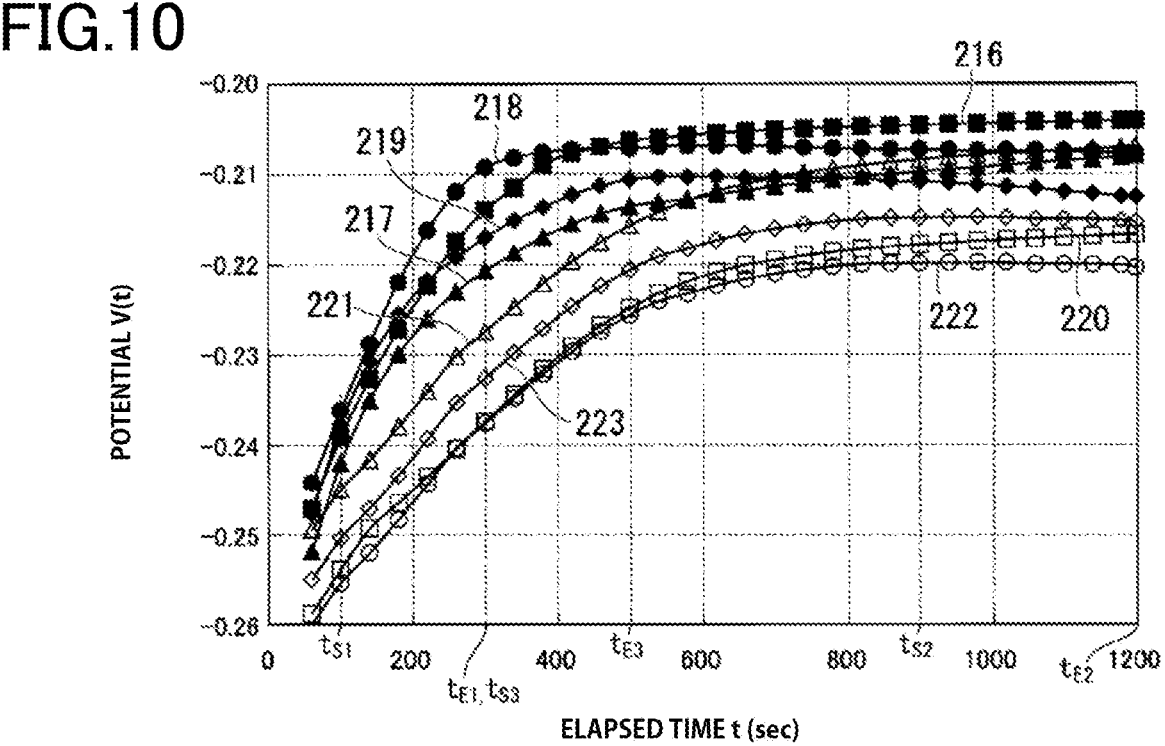
FIG. 10 is a schematic graph of a potential variation in the electroplating solution of Example 5.

FIG. 6 is a schematic graph of potential variations in the electroplating solution of Example 1. FIG. 7 is a schematic graph of potential variations in the electroplating solution of Example 2. FIG. 8 is a schematic graph of potential variations in the electroplating solution of Example 3. FIG. 9 is a schematic graph of potential variations in the electroplating solution of Example 4. FIG. 10 is a schematic graph of potential variations in the electroplating solution of Example 5.

In each graph, the horizontal axis indicates an elapsed time t (sec) and the vertical axis indicates a potential V(t) (V).

Note that the potential V(t) indicates a value with reference to a standard oxidation-reduction potential of copper.

Analyzed in Examples 1 to 5 were measurement samples of electroplating solutions 13 used in five plating devices (not shown) that were different from one another, and conditions of the measurement samples were determined by an electroplating solution analyzer 10.

<Measurement Samples>

Measurement samples P1 and P2 are samples of an electroplating solution 13 containing an identical type and concentration of additive, the samples being used in a first plating device. Metal ions contained in the measurement samples P1 and P2 are copper ions.

The measurement samples P1 and P2 were collected at different timings in an electroplating process with the first plating device. This means that the measurement samples P1 and P2 are used for periods of time different from each other. The accelerator and suppressor components of the additive contained in the measurement samples P1 and P2, therefore, each have a concentration different from each other.

Conditions of the measurement samples P1 and P2 are considered to be different from each other because these samples have been used for periods different from each other.

Measurement samples P3 and P4 were collected at different timings from the electroplating solution 13 used in a second plating device. The electroplating solution 13 used in the second plating device, however, has an additive type and concentration different from those of the electroplating solution 13 used in the first plating device. The types and concentrations of the accelerator and suppressor components contained in the additive of the unused electroplating solution 13 for the second plating device are therefore different from those of the accelerator and suppressor components contained in the additive the unused electroplating solution 13 for the first plating device.

Conditions of the measurement samples P3 and P4 are considered to be different from each other because these samples have been used for periods different from each other.

In the following description, if an unused electroplating solution 13 has a component of a different type or concentration, it is referred to merely as having a different component at an unused time, or before it is used.

The measurement samples P5, P6, and P7 were collected at different timings from an electroplating solution 13 used in a third plating device. However, the electroplating solution 13 used in the third plating device has different components when unused from those of the electroplating solutions 13 used in the first and second plating devices.

Conditions of the measurement samples P5, P6, and P7 are considered to be different from one another because these samples have been used for periods different from one another.

The measurement samples P8, P9, P10, P11, P12, P13, P14, and P15 were collected at different timings from an electroplating solution 13 used in a fourth plating device. An unused electroplating solution 13 for the fourth plating device, however, has components different from those of the electroplating solutions 13 used in the first to third plating devices.

Conditions of the measurement samples P8, P9, P10, P11, P12, P13, P14, and P15 are considered to be different from one another because these samples have been used for periods different from one another.

Measurement samples P16, P17, P18, P19, P20, P21, P22, and P23 were collected at different timings from the electroplating solution 13 used in a fifth plating device. An unused electroplating solution 13 for the fifth plating device, however, has a component that is different from that of the electroplating solution 13 used in the first to fourth plating devices.

Conditions of the measurement samples P16, P17, P18, P19, P20, P21, P22, and P23 are considered to be different from one another because these samples have been used for periods different from one another.

Example 1

In Example 1, the conditions of the measurement samples P1 and P2 were determined by use of the electroplating solution analyzer 10.

The specific configurations and measurement conditions of the electroplating solution analyzer 10 are as follows.

A platinum disk electrode is used as a working electrode 18. The platinum disk electrode has an area of 4 $\pi$mm$^2$.

An electrode formed from silver/silver chloride (Ag/AgCl) is used as a reference electrode 19. An electrode formed of a cylindrical copper ingot having a diameter of 8 mm is used as a counter electrode 21.

The measurement conditions of the potential V(t) in the potential measuring unit 28 are as follows: the working electrode 18 has a current density of 1 A/dm$^2$; the working electrode 18 rotates at 2500 rpm; and the measurement samples P1 and P2 are at 30° C. (303.15K) during measurement of the potential V(t).

The measurement data of the potential V(t) in Example 1 are indicated by a curve 201 ($\square$ symbols for the measurement sample P1) and a curve 202 ($\Delta$ symbols for the measurement sample P2) in FIG. 6. The measurement time $t_m$ is 1200 seconds.

Note that, in FIG. 6, the measurement data are thinned out for easier viewing, but the data are actually measured at intervals of one second. Measurement data whose elapsed time t is less than 50 seconds is not shown in the figure since they have a large fluctuation. This applies to the graphs in FIGS. 7 to 10, which will be described later.

A potential-variation rate $\Delta_1$ in a measurement section [100 secs, 300 secs] was used as an analysis value for determination of the electroplating solution 13 of Example 1. The equations (1) and (2) were used to calculate the potential-variation rate $\Delta_1$.

Example 1 is an example in which the potential-variation rate $\Delta_1$ is the only analysis value for determination.

In a condition for determination on the electroplating solution 13, a numerical value range to be satisfied by the potential-variation rate $\Delta_1$ is set to $R_1$[0.07 mV/sec, 0.10 mV/sec].

In Example 1, an individual evaluation value $EV_1$ relating to $\Delta_1$ also serves as an overall determination value $EV_T$.

Now a description will be given on an experiment with which the analysis value for determination and the determination condition in Example 1 were determined.

First, measurement data on the potential V(t) were obtained under conditions similar to those described above by use of a large number of various usage history samples of the electroplating solution 13 of Example 1. Then a via was actually electroplated by use of the individual samples.

In order to determine the determination condition, a via having a 100 μm diameter and a 70 μm depth was electroplated. Then via embeddability achieved by bottom-up deposition of the via was then evaluated by the depth of the via recessed as a result of the electroplating. In this evaluation, the via was determined to be well-embeddable if the post-electroplated via has a recessed depth that is 50% or less of the depth of the pre-electroplated via. Additionally, the via was determined not to be well-embeddable if the post-electroplated via has a recessed depth that is not 50% or less of the depth of the pre-electroplated via.

The temporal variation in the potential V(t) of a sample with good via embeddability was then compared with the temporal variation in the potential V(t) of a sample with poor via embeddability to determine a type of the analysis value for determination, a measurement section, and a determination condition from characteristics of the variations.

In Example 1, comparing the measurement data revealed that there was a small potential difference during a late period of potential measurement even if respective usage histories were different. The via embeddability was hence determined to correlate with a potential-variation rate during an initial period of potential measurement.

Then, in the measurement section corresponding to the initial period of potential measurement, the potential-variation rate was calculated to find the measurement section and the range of the potential-variation rate that provided the highest correlation with the evaluation on via embeddability, whereby the analysis value and determination condition described above were obtained.

Table 1 below shows potential-variation rates $\Delta_1$, which were calculated from the measurement data indicated by the curves 201 and 202, individual evaluation values $EV_1$ (overall determination values $EV_T$), and evaluation results on via embeddability.

In the column for the evaluation results on via embeddability, "OK" indicates good via embeddability whereas "NG" indicates poor via embeddability (this also applies to Tables 2 to 5).

TABLE 1

| Measurement Sample | Analysis Value for Determination $\Delta_1$ (mV/sec) | Individual Evaluation Value $EV_1$ | Overall Determination Value $EV_T$ | Via Embeddability |
|---|---|---|---|---|
| P1 | 0.124 | F | F | NG |
| P2 | 0.089 | T | T | OK |
| Numerical Value Range $R_s$ | [0.070, 0.100] | | | |

As shown in Table 1, in Example 1, the measurement sample P1 was determined to be in poor condition on a basis of the overall determination value $EV_T$. The measurement sample P2 was determined to be in a good condition. These determination results were consistent with the evaluations on via embeddability.

As described above, the electroplating solution analyzer 10 was able to accurately determine the condition of the electroplating solution 13 in Example 1.

Example 2

In Example 2, conditions of the measurement samples P3 and P4 were determined by use of the electroplating solution analyzer 10.

The specific configuration and measurement conditions of the electroplating solution analyzer 10 are similar to those of the above Example 1.

The measurement data of the potential V(t) in Example 2 are indicated by a curve 203 (□ symbols for the measurement sample P3) and a curve 204 (Δ symbols for the measurement sample P4) in FIG. 7. The measurement time $t_m$ is 1200 seconds.

An average potential $\mu_1$ in a measurement section [600 secs, 1200 secs] was used as an analysis value for determination on the electroplating solution 13 of Example 2. The equations (3) to (5) were used to calculate the average potential $\mu_1$.

Example 2 is an example in which the average potential $\mu_1$ is the only analysis value for determination.

In a condition for determination on the electroplating solution 13 of Example 2, a numerical value range to be satisfied by the average potential $\mu_1$ was set to $R_1$[−0.280 V, 0.260 V].

In Example 2, an individual evaluation value $EV_1$ relating to $\mu_1$ also serves as an overall determination value $EV_T$.

The analysis values for determination and the determination conditions in Example 2 were determined with an experiment similar to that in Example 1 by use of a large number of samples with various usage histories of the electroplating solution 13 of Example 2.

In Example 2, comparing the measurement data revealed that there was a small difference in potential-rate variation during an initial period of potential measurement even if respective usage histories were different. The via embeddability was hence determined to correlate with a potential during a late period of potential measurement.

Then, in the measurement section corresponding to the late period of potential measurement, an average potential was calculated to find the measurement section and the range of the average potential that provided the highest correlation with the evaluation on via embeddability, whereby the analysis value and determination condition described above were obtained.

Table 2 below shows average potentials $\mu_1$, which were calculated from the measurement data indicated by the curves 203 and 204, individual evaluation values $EV_1$ (overall determination values $EV_T$), and evaluation results on via embeddability.

TABLE 2

| Measurement Sample | Analysis Value for Determination $\mu_1$ (V) | Individual Evaluation Value $EV_1$ | Overall Determination Value $EV_T$ | Via Embeddability |
|---|---|---|---|---|
| P3 | 0.247 | F | F | NG |
| P4 | 0.268 | T | T | OK |
| Numerical Value Range $R_s$ | [−0.280, −0.260] | | | |

As shown in Table 2, in Example 2, the measurement sample P3 was determined to be in poor condition on a basis of the overall determination value $EV_T$. The measurement sample P4 was determined to be in a good condition. These determination results were consistent with the evaluations on via embeddability.

As described above, the electroplating solution analyzer 10 was able to accurately determine the condition of the electroplating solution 13 in Example 2.

Example 3

In Example 3, conditions of the measurement samples P5, P6, and P7 were determined by use of the electroplating solution analyzer 10.

The specific configuration and measurement conditions of the electroplating solution analyzer 10 are similar to those of the above Example 1.

The measurement data of the potential V(t) in Example 3 are indicated by a curve 205 (□ symbols for the measurement sample P5), a curve 206 (Δ symbols for the measurement sample P2), and a curve 207 (○ symbols, measurement sample P7) in FIG. 8. The measurement time $t_m$ is 1200 seconds.

A potential-variation rate $\Delta_1$ in a measurement section [100 secs, 300 secs] and an average potential $\mu_1$ in a measurement section [700 secs, 1200 secs] were used as an analysis value for determination on the electroplating solution 13 of Example 3.

The equations (1) and (2) were used to calculate the potential-variation rate $\Delta_1$. The equations (3) to (5) were used to calculate the average potential $\mu_1$.

Example 3 is an example in which the analysis values for determination are the potential-variation rate $\Delta_1$ and the average potential $\mu_1$.

In a condition for determination on the electroplating solution 13 of Example 3, a numerical value range to be satisfied by the potential-variation rate $\Delta_1$ was set to $R_3$[0.050 mV/sec, 0.100 mV/sec]. Additionally, a numerical value range to be satisfied by the average potential $\mu_1$ was set to $R_2$[−0.150 V, −0.140 V].

In Example 3, the overall determination value $EV_T$ was determined to be T when at least one of the individual determination value $EV_1$ regarding $\Delta_1$ and the individual determination value $EV_2$ regarding $\mu_1$ is T. In other words, in Example 3, the overall determination value $EV_T$ was determined to be T when ($EV_1$, $EV_2$) is one of (T,T), (T,F), and (F,T).

The analysis values for determination and the determination conditions in Example 3 were determined with an experiment similar to that in Example 1 by use of a large number of samples with various usage histories of the electroplating solution 13 of Example 3.

In Example 3, comparing the measurement data resulted in a determination that the combination of a potential-variation rate during an initial period of potential measurement and a potential during a late period of potential measurement correlated with via embeddability depending on usage history.

Then calculating a potential-variation rate and an average potential in each of the measurement sections corresponding to the initial and late periods of potential measurement to find the measurement section, potential-variation rate, and average potential that provided the highest correlation with the evaluation on via embeddability yielded the above analysis value and determination condition.

Table 3 below shows potential-variation rates $\Delta_1$, which were calculated from the measurement data indicated by the curves 205, 206, and 207, average potentials $\mu_1$, individual evaluation values $EV_1$, $EV_2$, overall determination values $EV_T$, and evaluation results on via embeddability.

TABLE 3

| Measurement Sample | Analysis Value for Determination | | Individual Evaluation Value | | Overall Determination Value $EV_T$ | Via Embeddability |
|---|---|---|---|---|---|---|
| | $\Delta_1$ (mV/sec) | $\mu_1$ (V) | $EV_1$ | $EV_2$ | | |
| P5 | 0.123 | −0.135 | F | F | F | NG |
| P6 | 0.127 | −0.146 | F | T | T | OK |
| P7 | 0.083 | −0.136 | T | F | T | OK |
| Numerical Value Range $R_s$ | [0.050, 0.100] | [−0.150, −0.140] | | | | |

As shown in Table 3, in Example 3, the measurement sample P5 was determined to be in poor condition on a basis of the overall determination value $EV_T$. The measurement samples P6 and P7 were determined to be in a good condition. These determination results were consistent with the evaluations on via embeddability.

As described above, the electroplating solution analyzer 10 was able to accurately determine the condition of the electroplating solution 13 in Example 3.

Example 4

In Example 4, conditions of the measurement samples P8, P9, P10, P11, P12, P13, P14, and P15 were determined by use of the electroplating solution analyzer 10.

The specific configuration and measurement conditions of the electroplating solution analyzer 10 are similar to those of the above Example 1.

The measurement data of the potential V(t) in Example 4 are indicated by a curve 208 (■ symbols for the measurement sample P8), a curve 209 (▲ symbols for the measurement sample P9), a curve 210 (● symbols for the measurement sample P10), a curve 211 (♦ symbols for the measurement sample P11), a curve 212 (symbols for the measurement sample P12), a curve 213 (Δ symbols for the measurement sample P13), a curve 214 (○ symbols for the measurement sample P14), and a curve 215 (◇ symbols for the measurement sample P15) in FIG. 9. The measurement time $t_m$ is 1200 seconds.

A potential-variation rate $\Delta_1$ in the measurement section [100 secs, 300 secs], an average potential $\mu_1$ in the measurement section [400 secs, 800 secs], and an average potential $\mu_2$ in the measurement section [800 secs, 1200 secs] were used as analysis values for determination on the electroplating solution 13 of Example 4.

The equations (1) and (2) were used to calculate the potential-variation rate $\Delta_1$. The equations (3) to (5) were used to calculate the average potentials $\mu_1$ and $\mu_2$.

Example 4 is an example in which analysis values for determination are the potential-variation rate $\Delta_1$ and the average potentials $\mu_1$ and $\mu_2$.

In a condition for determination on the electroplating solution 13 of Example 4, a numerical value range to be satisfied by the potential-variation rate $\Delta_1$ was set to $R_1$[0.050 mV/sec, 0.100 mV/sec]. A numerical value range to be satisfied by the average potential $\mu_1$ was set to $R_2$[−0.250 V,−0.240 V]. A numerical value range to be satisfied by the average potential $\mu_2$ was set to $R_3$[−0.250 V,−0.240 V].

In Example 4, the overall determination value $EV_T$ was determined to be T if ($EV_1$, $EV_2$, $EV_3$) is one of (T, T, T), (T, T, F), (T, F, T), and (F, T, T). On the other occasions, the overall determination value $EV_T$ was determined to be F.

Relations between respective individual evaluation values and overall determination values may be determined as appropriate. In Example 4, the overall determination value $EV_T$ was determined to be T if two or more of the individual evaluation values $EV_1$, $EV_2$, and $EV_3$ is T.

In other words, the overall determination value $EV_T$ was determined to be T if ($EV_1$, $EV_2$, $EV_3$) is one of (T, T, T), (T, T, F), (T, F, T), and (F, T, T). On the other occasions, the overall determination value $EV_T$ was determined to be F.

The analysis values for determination and the determination conditions in Example 4 were determined with an experiment similar to that in Example 1 by use of a large number of samples with various usage histories of the electroplating solution 13 of Example 4.

In Example 4, comparing the measurement data resulted in a determination that the combination of a potential-variation rate during an initial period of potential measurement and a potential during middle and late periods of potential measurement correlated with via embeddability depending on usage history.

Then, in each of the measurement sections corresponding to the initial, middle, and late periods of potential measurement, a potential-variation rate and an average potential were calculated to find a measurement section, potential-variation rate, and range of the average potential that provided the highest correlation with the evaluation on via embeddability. The analysis values and determination conditions described above were thereby obtained.

Table 4 below shows potential-variation rates $\Delta_1$ and average potentials $\mu_1$, $\mu_2$, which were calculated from the measurement data indicated by the curves 208, 209, 210, 211, 212, 213, 214, and 215, respective individual evaluation values $EV_1$, $EV_2$, $EV_3$, overall determination values $EV_T$, and evaluation results on via embeddability.

TABLE 4

| Measurement Sample | Analysis Value for Determination | | | Individual Evaluation Value | | | Overall Determination Value $EV_T$ | Via Embeddability |
|---|---|---|---|---|---|---|---|---|
| | $\Delta_1$ (mV/sec) | $\mu_1$ (V) | $\mu_2$ (V) | $EV_1$ | $EV_2$ | $EV_3$ | | |
| P8 | 0.123 | −0.237 | −0.235 | F | F | F | F | NG |
| P9 | 0.104 | −0.239 | −0.241 | F | F | T | F | NG |
| P10 | 0.106 | −0.242 | −0.239 | F | T | F | F | NG |
| P11 | 0.136 | −0.242 | −0.242 | F | T | T | T | OK |
| P12 | 0.087 | −0.238 | −0.233 | T | F | F | F | NG |

TABLE 4-continued

| Measurement Sample | Analysis Value for Determination | | | Individual Evaluation Value | | | Overall Determination Value $EV_T$ | Via Embeddability |
|---|---|---|---|---|---|---|---|---|
| | $\Delta_1$ (mV/sec) | $\mu_1$ (V) | $\mu_2$ (V) | $EV_1$ | $EV_2$ | $EV_3$ | | |
| P13 | 0.083 | −0.251 | −0.245 | T | F | T | T | OK |
| P14 | 0.089 | −0.243 | −0.238 | T | T | F | T | OK |
| P15 | 0.082 | −0.245 | −0.241 | T | T | T | T | OK |
| Numerical Value Range $R_s$ | [0.050, 0.100] | [−0.240, −0.250] | [−0.240, −0.250] | | | | | |

In Example 4, the measurement samples P8, P9, P10, and P12 were determined to be in poor condition on a basis of the overall determination values $EV_T$, as shown in Table 4, The measurement samples P11, P13, P14, and P15 were determined to be in a good condition. These determination results were consistent with the evaluations on via embeddability.

In Example 4, the electroplating solution analyzer 10 was thus able to accurately determine the condition of the electroplating solution 13.

Example 5

In Example 5, the conditions of the measurement samples P16, P17, P18, P19, P20, P21, P22, and P23 were determined by use of the electroplating solution analyzer 10.

The specific configuration and measurement conditions of the electroplating solution analyzer 10 are similar to those of the above Example 1.

The measurement data of the potential V(t) in Example 5 are indicated by a curve 216 (■ symbols for the measurement sample P16), a curve 217 (▲ symbols for the measurement sample P17), a curve 218 (● symbols for the measurement sample P18), a curve 219 (♦ symbols for the measurement sample P19), a curve 220 (symbols for the measurement sample P20), a curve 221 (Δ symbols for the measurement sample P21), a curve 222 (○ symbols for the measurement sample P22), and a curve 223 (◊ symbols for the measurement sample P23) in FIG. 10. The measurement time $t_m$ is 1200 seconds.

A potential-variation rate $\Delta_1$ in the measurement section [100 secs, 300 secs], a potential-variation rate $\Delta_2$ in the measurement section [900 secs, 1200 secs], and an average potential $\mu_1$ in the measurement section [300 secs, 500 secs] were used as an analysis value for determination on the electroplating solution 13 of Example 5.

The equations (1) and (2) were used to calculate the potential-variation rate $\Delta_1$ and $\Delta_2$. The equations (3) to (5) were used to calculate the average potential $\mu_1$.

Example 5 is an example in which analysis values for determination are the potential-variation rate $\Delta_1$, $\Delta_2$ and the average potential $\mu_1$.

In a determination condition for determining the electroplating solution 13 of Example 5, a numerical value range to be satisfied by the potential-variation rate $\Delta_1$ was set to $R_1$[0.05 mV/sec, 0.10 mV/sec], a numerical value range to be satisfied by the potential-variation rate $\Delta_2$ was set to $R_2$[−0.10 mV/sec, 0.00 mV/sec], and a numerical value range to be satisfied by the average the potential $\mu_1$ was set to $R_3$[−0.230 V, −0.210 V].

In Example 5, the overall determination value $EV_T$ is determined to be T if ($EV_1$, $EV_2$, $EV_3$) is one of (T,T,T), (T,F,T), and (F,T,T). On the other occasions, the overall determination value $EV_T$ is determined to be F.

Relations between respective individual evaluation values and overall determination values may be determined as appropriate. In Example 5, the overall determination value $EV_T$ was determined to be T if one or more of the individual evaluation values $EV_1$ and $EV_2$ is T and $EV_3$ is T. In other words, the overall determination value $EV_T$ was determined to be T if ($EV_1$, $EV_2$, $EV_3$) is one of (T, T, T), (T, F, T), and (F, T, T). On the other occasions, the overall determination value $EV_T$ was determined to be F.

The analysis values for determination and the determination conditions in Example 5 were determined with an experiment similar to that in Example 1 by use of a large number of samples with various usage histories of the electroplating solution 13 of Example 5.

In Example 5, comparing the measurement data resulted in a determination that the combination of a potential-variation rate during initial and late periods of potential measurement and a potential during a middle period of potential measurement correlated with via embeddability depending on usage histories.

Then, in each of various measurement sections corresponding to the initial, middle, and late periods of potential measurement, a potential-variation rate and an average potential were calculated to find a measurement section, potential-variation rate, and range of the average potential that provided the highest correlation with the evaluation on via embeddability. The analysis values and determination conditions described above were thereby obtained.

Table 5 below shows potential-variation rates $\Delta_1$ and $\Delta_2$, and average potentials $\mu_1$, which were calculated from the measurement data indicated by the curves 216, 217, 218, 219, 220, 221, 222, and 223, respective individual evaluation values $EV_1$, $EV_2$, $EV_3$, an overall determination value $EV_T$, and evaluation results on via embeddability.

TABLE 5

| Measurement Sample | Analysis Value for Determination Δ₁ (mV/sec) | Δ₂ (mV/sec) | $\mu_1$ (V) | Individual Evaluation Value EV₁ | EV₂ | EV₃ | Overall Determination Value EV$_T$ | Via Embeddability |
|---|---|---|---|---|---|---|---|---|
| P16 | 0.126 | −0.001 | −0.209 | F | F | F | F | NG |
| P17 | 0.106 | −0.002 | −0.217 | F | F | T | F | NG |
| P18 | 0.135 | −0.001 | −0.208 | F | T | F | F | NG |
| P19 | 0.103 | −0.002 | −0.213 | F | T | T | T | OK |
| P20 | 0.083 | −0.001 | −0.232 | T | F | F | F | NG |
| P21 | 0.087 | −0.001 | −0.221 | T | F | T | T | OK |
| P22 | 0.089 | −0.001 | −0.231 | T | T | F | F | NG |
| P23 | 0.089 | −0.001 | −0.226 | T | T | T | T | OK |
| Numerical Value Range R$_s$ | [0.050, 0.100] | [−0.010, 0.000] | [−0.230, −0.210] | | | | | |

In Example 5, the measurement samples P16, P17, P18, P20, and P22 were determined to be in poor condition on a basis of the overall determination value EV$_T$, as shown in Table 5. The measurement samples P19, P21, and P23 were determined to be in a good condition. These determination results were consistent with the evaluations on via embeddability.

In Example 5, the electroplating solution analyzer 10 was thus able to accurately determine the condition of the electroplating solution 13.

INDUSTRIAL APPLICABILITY

The present invention can be applied to an electroplating solution analyzer, which is an analyzing device for an electroplating solution to be used in a variety of applications such as decoration, copper foil manufacturing, and electronic components, and to an electroplating solution analysis method. The invention can be applied in particular to an electroplating solution analyzer, which is an analyzing device for an electroplating solution to be used at a time of formation of a conductor on a high-density mounting board, a semiconductor package substrate, and a contact via or via-hole formed on a semiconductor substrate, and to an electroplating solution analysis method.

REFERENCE SYMBOLS LIST

10 . . . Electroplating solution analyzer; 11 . . . Stand; 11A . . . Stage unit; 12 . . . Analysis container; 13 . . . Electroplating solution; 15 . . . Temperature holding unit; 16 . . . Electrode support unit; 18 . . . Working electrode; 19 . . . Reference electrode; 21 . . . Counter electrode; 23 . . . Rotation drive unit; 25 . . . Controller; 26 . . . Current-generating unit; 28 . . . Potential measurement unit; 31 . . . Analyzing unit; 42 . . . Main analysis body; 43 . . . Display; 44 . . . Keyboard; E$_s$ . . . Analysis value for determination; EV$_s$ . . . Individual evaluation value; EV$_T$ . . . Overall determination value; R$_s$ . . . Numeric value range; t . . . Elapsed time; V(t) . . . Potential; $\Delta_j$ . . . Potential-variation rate (analysis value for determination); $\mu_k$ . . . Average potential (analysis value for determination).

What is claimed is:

1. A method for determining a condition of an electroplating solution by:
   immersing a working electrode, a reference electrode, and a counter electrode in an electroplating solution containing additives including an accelerator and a suppressor, and rotating the working electrode at a constant speed;
   supplying a current with a constant current density between the working electrode and the counter electrode to measure a potential between the working electrode and the reference electrode as a function of an elapsed time after the current starts to be supplied;
   calculating an analysis value comprising a potential-variation rate and an average potential, wherein the potential-variation rate is calculated in a first elapsed time section and the average potential is calculated in a second elapsed time section, which is later than the first elapsed time section; and
   evaluating the analysis value on a basis of a preset determination condition.

2. The method of claim 1, wherein the first elapsed time section does not overlap with the second elapsed time section.

3. The method of claim 1, wherein the first elapsed time section is from 100 sec to 300 sec and the second elapsed time section is from 700 sec to 1200 sec.

4. The method of claim 1, wherein the analysis value comprises the potential-variation rate calculated at the first elapsed time section, a first average potential calculated at the second elapsed time section and a second average potential calculated at a third elapsed time section, which is later than the second elapsed time section.

5. The method of claim 1, wherein the analysis value comprises a first potential-variation rate calculated at the first elapsed time section, the average potential calculated at the second elapsed time section and a second potential variation rate calculated at a third elapsed time section, which is later than the first elapsed time section.

6. The method of claim 5, wherein the third elapsed time section is earlier than the second elapsed time section.

7. A method for determining a condition of an electroplating solution by:
   immersing a working electrode, a reference electrode, and a counter electrode in an electroplating solution containing additives including an accelerator and a suppressor, and rotating the working electrode at a constant speed;
   supplying a current with a constant current density between the working electrode and the counter electrode to measure a potential between the working electrode and the reference electrode as a function of an elapsed time after the current starts to be supplied;

calculating an analysis value comprising more than one potential-variation rates and/or more than one average potentials, wherein the potential-variation rates are calculated in multiple first elapsed time sections, and the average potentials are calculated in multiple second elapsed time sections, which are later in time than the first elapsed sections; and evaluating the analysis value for determination on a basis of a preset determination condition.

* * * * *